US007294340B2

(12) United States Patent
Sung et al.

(10) Patent No.: US 7,294,340 B2
(45) Date of Patent: Nov. 13, 2007

(54) HEALTHCARE AND COSMETIC COMPOSITIONS CONTAINING NANODIAMOND

(75) Inventors: Chien-Min Sung, No. 4, Lane 32, Chung-Cheng Road, Tansui, Taipei County (TW) 23911; Michael Sung, Cambridge, MA (US); Emily Sung, Santa Clara, CA (US)

(73) Assignee: Chien-Min Sung, Tansui (TW)

( * ) Notice: Subject to any disclaimer, the term of this patent is extended or adjusted under 35 U.S.C. 154(b) by 403 days.

(21) Appl. No.: 10/814,660

(22) Filed: Mar. 30, 2004

(65) Prior Publication Data

US 2005/0220829 A1   Oct. 6, 2005

(51) Int. Cl.
*A61K 8/02* (2006.01)
*A61L 9/01* (2006.01)
*A61Q 1/00* (2006.01)
*A61Q 3/00* (2006.01)
*A61Q 5/02* (2006.01)

(52) U.S. Cl. .................. 424/401; 424/422; 424/70.1; 424/76.1; 424/61

(58) Field of Classification Search ................ 424/401, 424/422, 70.1, 76.1, 61
See application file for complete search history.

(56) References Cited

U.S. PATENT DOCUMENTS

| | | | |
|---|---|---|---|
| 3,944,506 A | 3/1976 | Hramchenko et al. | |
| 4,048,123 A | 9/1977 | Hramchenko et al. | |
| 4,414,199 A | 11/1983 | Strobridge | |
| 4,482,538 A * | 11/1984 | Davies ........................ | 424/61 |
| 4,737,307 A | 4/1988 | Brown et al. | |
| 5,326,483 A | 7/1994 | Halloran et al. | |
| 5,709,577 A | 1/1998 | Jin et al. | |
| 5,725,866 A | 3/1998 | Ramin | |
| 5,882,636 A | 3/1999 | Mui et al. | |
| 5,968,490 A | 10/1999 | Sun et al. | |
| 5,985,300 A | 11/1999 | Crotty et al. | |
| 6,004,539 A | 12/1999 | Longo, Jr. et al. | |
| 6,020,395 A | 2/2000 | Angeletakis | |
| 6,106,818 A | 8/2000 | Dulog et al. | |
| 6,117,415 A | 9/2000 | Schwarz | |
| 6,121,344 A | 9/2000 | Angeletakis | |
| 6,123,925 A | 9/2000 | Barry et al. | |
| 6,156,325 A | 12/2000 | Farer et al. | |
| 6,187,327 B1 | 2/2001 | Stack | |
| 6,207,175 B1 | 3/2001 | Lebreton | |
| 6,248,339 B1 | 6/2001 | Knitowski et al. | |
| 6,306,805 B1 | 10/2001 | Bratescu et al. | |
| 6,352,687 B1 | 3/2002 | Ismailer et al. | |
| 6,358,499 B2 | 3/2002 | Hall-Puzio et al. | |
| 6,428,794 B1 | 8/2002 | Klofta et al. | |
| 6,500,183 B1 | 12/2002 | Waldrom | |
| 6,503,488 B1 | 1/2003 | Rosen et al. | |
| 6,518,228 B1 | 2/2003 | Jorgensen et al. | |
| 6,579,516 B1 | 6/2003 | Mansouri | |
| 6,593,395 B2 | 7/2003 | Angeletakis et al. | |
| 6,607,719 B2 | 8/2003 | Uemura et al. | |
| 2003/0032693 A1 | 2/2003 | Angeletakis et al. | |
| 2003/0049291 A1 | 3/2003 | Cheski | |
| 2003/0059389 A1 | 3/2003 | Tournihac et al. | |
| 2003/0064086 A1 | 4/2003 | Carrion et al. | |
| 2003/0165550 A1 | 9/2003 | Rhoades | |
| 2003/0211954 A1 | 11/2003 | Kono et al. | |

OTHER PUBLICATIONS

Raty, J. et al., "Ultradispersity of diamond at the nanoscale", Nature Materials, vol. 2, Dec. 2003, Nature Publishing Group, pp. 792-5.*
Flick, E. Cosmetic Additive, 1991, Noyes Publications p. 635.*
Ritter, Mindy, "Nanoparticles—What's Now, What's Next?" Chemical Engineering Progress, 39S-42S, Nov. 2003.
Xu, Kang and Qunji Xue, "A New Method for Deaggregation of Nanodiamond from Explosive Detonation: Graphitization-Oxidation Method," Physics of the Solid State, 2004, vol. 46, No. 4.

* cited by examiner

*Primary Examiner*—Sreeni Padmanabhan
*Assistant Examiner*—Gina Yu
(74) *Attorney, Agent, or Firm*—Thorpe North & Western LLP

(57) ABSTRACT

Nanodiamonds can be included in various compositions to take advantage of the ability of nanodiamond to bond with biological materials and to improve mechanical strength. Nanodiamonds can be dispersed in a biologically acceptable carrier to form various nanodiamond compositions. The presence of nanodiamonds can increase binding with many biological materials, making the compositions of the present invention useful for a large variety of purposes such as cleansing, testing and identification of materials, and treatment of adverse conditions. Specific examples of nanodiamond compositions that can be formulated include deodorants, toothpastes, shampoos, antibiotics, dermal strips, DNA test strips, skin cleansers, and the like. Similarly, nanodiamond particles can be included in a cosmetic nanodiamond composition within a cosmetically acceptable carrier. Cosmetic nanodiamond compositions can include, for example, nail polish, eyeliner, lip gloss, exfoliant, and the like.

27 Claims, No Drawings

HEALTHCARE AND COSMETIC COMPOSITIONS CONTAINING NANODIAMOND

FIELD OF THE INVENTION

The present invention relates to cosmetic and remedial health compositions and to methods for the preparation thereof. Accordingly, the present invention involves the fields of chemistry, healthcare, materials science, and cosmetics.

BACKGROUND OF THE INVENTION

Diamond is the hardest material known and is commonly used as a superabrasive for removing excess materials. Typical superabrasive products include diamond saws, grinding wheels, polishing pads and the like. Diamond superabrasives have been commercially available in a number of mesh sizes. For example, diamond saws typically incorporate diamond particles having a U.S. mesh size of 18 (about 1 mm) to 60 (about 0.25 mm). Grinding applications often employ diamond particles having a size of 60 to 400 (about 37 microns) U.S. mesh, while polishing applications typically require diamond fines down to about 0.1 micron. Until recently, diamond particles smaller than about 100 nm were not commercially available.

Diamond micron powders are commonly made by pulverizing waste diamond grains that are not otherwise suitable for ultrafine polishing where nanometer scale smoothness is desired. Further, typical pulverized diamond particles include sharp corners and irregular shapes which are not suitable for polishing of expensive workpieces such as silicon wafers, integrated circuitry, and the like. Most expensive workpieces are currently polished using conventional abrasives such as silicon carbide and aluminum oxide.

In addition, it is typically not commercially feasible to pulverize diamond waste to particle sizes below 100 nm. Moreover, very fine diamond particles are too small to be sized by sieving as they tend to plug the screen holes. Hence, sedimentation has been the primary technique to sort diamond fines by size. Sedimentation techniques can take over a week when particle sizes are smaller than 100 nm, however, can be accelerated somewhat using centrifugal force.

Most diamond superabrasives are synthesized from graphite under ultrahigh pressure (e.g. 5.5 GPa) using molten metal (e.g., Fe, Ni, Co or their alloys) as catalyst. Under conditions of high temperature and high pressure, graphite is dissolved or dispersed in the molten catalyst and precipitates out as diamond. The growth rate of a diamond crystal is partially dependent on the pressure and temperature, and can be as fast as about 1 mm per hour. Typically, the materials in a diamond growth reaction cell are not sufficiently uniform to allow precise control of diamond growth. Moreover, the pressure and temperatures have large gradients which vary during diamond synthesis. Consequently, it would not be practical to grow diamond having a size smaller than a few microns.

An alternative method to grow micron sized diamond is by compressing graphite with a shock wave. Graphite powder can be mixed with a cooling metal (e.g. Cu) powder and the mixture is sealed in a steel tube. The tube is then surrounded by an explosive that is capable of generating a shock wave through the tube when ignited. In this case, a high pressure is maintained for merely about one microsecond. The diamond grains thus formed are typically several microns in size. However, these grains are polycrystalline in nature.

In recent years, nanoparticles of diamond have become commercially available. Such nanodiamond particles are commonly formed by explosion. However, instead of graphite being compressed with a shock wave, the dynamite (e.g. TNT and RDX mixture) itself is converted to nanodiamond during less than a microsecond when both the pressure and temperature are high, i.e. over 20 GPa and 3000° C. Nanodiamonds so formed are typically smaller than 10 nm (e.g. 5 nm) and tend to have a very narrow size distribution, i.e. from about 4 nm to about 10 nm. Moreover, the surface of these nanodiamonds contains diamond or diamond-like carbon, such as bucky balls (C60), layered shells, carbon nanotubes, and amorphous carbon. Thus, these nanodiamonds are extremely hard without sharp corners.

Nanodiamond has been used as abrasives for the ultra-fine polishing of hard materials (e.g. gems), hardening wear resistant coatings (e.g. Cr coatings), strengthening soft materials (e.g. rubber), and as a mechanical lubricant (e.g. engine oil additive). However, the properties and applications of nanodiamond particles continue to be explored.

As a result, compositions and methods of using nanodiamond which improve desirable properties of various compositions continue to be sought.

SUMMARY OF THE INVENTION

To this point, there has been no report on the usefulness of nanodiamond in binding to biological materials or for making cosmetic or healthcare products. Hence, one purpose of this invention is to use nanodiamond in various compositions to take advantage of the ability of nanodiamond to bond with biological materials and to improve mechanical strength. Further, the diamond-like carbon coatings of some nanodiamonds can provide beneficial properties for healthcare applications. For example, nanodiamonds can be added to healthcare compositions or cosmetics for affecting the appearance of the human body, such as in skin care (e.g. cleansers, facial tissue), nail protection (e.g. nail polish), or dental reconstruction (e.g. cavity filling). Similarly, nanodiamonds can be added to lotions, dermal strips, shampoo, toothpaste, or used in a deodorant.

In one general aspect of the present invention, a method of binding biological molecules can include formulating a nanodiamond composition and placing the composition in contact with biological material. The nanodiamond composition can include a plurality of nanodiamond particles dispersed in a biologically acceptable carrier. Due to the binding properties of nanodiamonds, at least a portion of the biological material can be bonded to the nanodiamond composition. Examples of biological material which can be bonded to nanodiamonds include organic oils, sebum, bacteria, epithelial cells, amino acids, proteins, DNA, and the like. As such, the nanodiamond compositions of the present invention can be useful for a large variety of purposes such as cleansing, testing and identification of materials, and treatment of adverse conditions. Specific examples of nanodiamond compositions that can be formulated include deodorants, toothpastes, shampoos, antibiotics, dermal strips, DNA test strips, skin cleansers, and the like.

In one detailed aspect, a remedial healthcare nanodiamond composition can include a biologically acceptable carrier and a plurality of nanodiamond particles dispersed in the carrier. Examples of such remedial healthcare compositions can include without limitation, dental fillings, lotions, deodorants, antibiotics, dermal strips, skin cleansers, and exfoliants.

In another detailed aspect of the present invention, the remedial composition can include nanodiamond particles at from about 1 wt % to about 80 wt % of the composition. The nanodiamonds can have an average size from about 0.5 nm to about 50 nm, and in some aspects can have an average size from about 0.5 nm to about 8 nm.

In still another aspect, nanodiamond particles can be included in a cosmetic nanodiamond composition within a cosmetically acceptable carrier. Cosmetic nanodiamond compositions can include, for example, nail polish, eyeliner, lip gloss, exfoliant, and the like.

In one aspect of the present invention, the nanodiamond compositions can include additives as required to create a specific formulation, such as dispersant, pigment, plasticizer, bubbling agent, solvent, stabilizer, and combinations thereof. These additives can provide a wide variety of advantages, depending on the specific formulation. For example, bubbling agents can be used to improve contact of biological material with unsaturated nanodiamond particles.

There has thus been outlined, rather broadly, various features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

DETAILED DESCRIPTION OF THE INVENTION

Definitions

In describing and claiming the present invention, the following terminology will be used in accordance with the definitions set forth below.

The singular forms "a," "an," and "the" include plural referents unless the context clearly dictates otherwise. Thus, for example, reference to "a solvent" includes reference to one or more of such solvents, and reference to "the dispersant" includes reference to one or more of such dispersants.

As used herein, "formulation" and "composition" may be used interchangeably and refer to a combination of elements that is presented together for a given purpose. Such terms are well known to those of ordinary skill in the art.

As used herein, "carrier," "inert carrier," and "acceptable carrier" may be used interchangeably and refer to a carrier which may be combined with a plurality of nanodiamond particles in order to provide a desired composition. Those of ordinary skill in the art will recognize a number of carriers that are well known for making specific remedial healthcare and/or cosmetic compositions.

As used herein, "cosmetically acceptable carrier" refers to a material which is suitable for application to keratinous surfaces or other areas of the body. Upon application, cosmetically acceptable carriers are substantially free of adverse reactions with skin and other keratinous surfaces.

As used herein, "biologically acceptable carrier" refers to a material which is suitable for use in connection with a particular biological material. A biologically acceptable carrier is compatible with, and does not adversely affect, a biological material or subject contacted therewith under prescribed conditions.

As used herein, "cosmetic" is an adjective referring to improving the appearance of a surface or covering defects. Typically, cosmetic compositions can be used to improve aesthetic rather than functional aspects of a surface. Most commonly, cosmetic compositions are formulated for application as a health and beauty treatment or for affecting personal appearance of the body, for example, keratinous surfaces such as skin, hair, nails, and the like.

As used herein, "remedial" is an adjective referring to remedying, correcting, treating, improving, or preventing an undesirable condition. A remedial composition can therefore be formulated to remove undesirable materials such as sebum, dead skin, and the like from the skin. Similarly, remedial compositions can be configured to remove, prevent or minimize formation of undesirable elements such as odor-producing bacteria and the like. Alternatively, remedial compositions can remedy a structural defect such as in dental reconstruction or as a cavity filler material.

As used herein, "biological material" refers to any material which is a product of a biological organism. Typical biological materials of interest can include organic oils, sebum, bacteria, epithelial cells, amino acids, proteins, DNA, and the like.

As used herein, "bonded" and "bonding," when used in connection with nanodiamond contact with biological materials, refers to bonding such as covalent bonding, ionic bonding, mechanical bonding, van der Waals attractions, hydrogen bonding, or other intermolecular attractive forces.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a range of 1 to 5 should be interpreted to include not only the explicitly recited limits of 1 and 5, but also to include individual values such as 2, 2.7, 3.6, 4.2, and sub-ranges such as 1-2.5, 1.8-3.2, 2.6-4.9, etc. This interpretation should apply regardless of the breadth of the range or the characteristic being described, and also applies to open-ended ranges reciting only one end point, such as "greater than 25," or "less than 10".

The Invention

The present invention provides compositions containing nanodiamond particles. More specifically, nanodiamond particles can be included in remedial healthcare and cosmetic compositions to provide a number of advantages. The presence of nanodiamond particles can enhance mechanical properties, as well as provide improved bonding of certain biological materials.

In one embodiment, a remedial healthcare nanodiamond composition can include a biologically acceptable carrier and a plurality of nanodiamond particles dispersed in the carrier. Depending on the carrier, an optional dispersant can be used. The remedial healthcare composition can be formulated as a dental filling, lotion, deodorant, toothpaste, shampoo, antibiotic, dermal strip, skin cleanser, or exfoliant. Other similar compositions can also be formulated to incorporate nanodiamond particles given the disclosure herein. Of course, the particular biologically acceptable carriers and other components may vary depending on the specific formulation. However, the following discussion illustrates several currently preferred nanodiamond compositions and associated benefits.

Nanodiamond particles typically carry an electrical charge which leads to aggregation and flocculation of particles. In most cases, this aggregation of nanodiamond particles is undesirable. Therefore, an optional dispersant can be included which improves the uniformity of nanodiamond distribution. In this way, a colloidal suspension can be formed in which the nanodiamond particles remain substantially uniformly dispersed over an extended period of time, e.g., typically months or years. Preferably, the nanodiamond particles remain dispersed during the useful shelf-life of the particular composition. The dispersant can be provided in the form of a specific compound separate from the carrier in a liquid nanodiamond composition. However, for highly viscous compositions the carrier can also be the dispersant. Thus, in some embodiments such as a solid deodorant, toothpaste, soaps, viscous nail polish, and the like, the carrier can provide sufficient viscous support to prevent agglomeration and/or settling of the nanodiamond particles.

Any suitable dispersant can be used which is compatible with a particular carrier. However, several non-limiting examples of dispersants include anionic surfactants, electrolytes, alcohols, metal chlorides and nitrates such as Al, Na, Ca, and Fe chlorides and nitrates, and the like. Other suitable nanodiamond dispersants include isopropyl triisosteroyl titanate, polyethylene-oxides, and other anionic surfactants. One specific suitable surfactant which can be used is stearalkonium hectorite. The dispersant can also provide other properties to a composition such as pH control. Further, the amount of dispersant can depend on the amount of nanodiamond present and the viscosity of the composition. However, as a general guideline, the remedial healthcare composition can include from 1 wt % to about 30 wt % dispersant.

The compositions of the present invention can include a plurality of nanodiamond particles. Suitable nanodiamond particles can have an average size of from about 0.5 nm to about 50 nm. In some embodiments the plurality of nanodiamond particles can have an average size from 1 nm to about 10 nm, preferably from about 4 nm to about 8 nm, and most preferably about 5 nm. The concentration of nanodiamond particles will vary depending on the composition and the desired effect, as discussed in more detail below. As a practical matter, the plurality of nanodiamond particles is typically about 1 wt % to about 80 wt % of the composition. Nanodiamond particles can be formed using a number of known techniques such as shock wave synthesis, CVD, and the like. Currently preferred nanodiamond particles are produced by shock wave synthesis.

In one embodiment of the present invention, the remedial healthcare composition is formulated as a dental material. The dental material can be formulated for use as a filling, veneer, reconstruction, and the like. The dental material can include an acceptable carrier and a plurality of nanodiamond particles. Acceptable carriers are known in the art and can include, for example, composite resins, polymeric resins, ceramics, and other known carriers. In addition, the dental material can include additives such as colorants, fillers, etc. Although dental compositions can include colorants or additives to provide whiteness for cosmetic purposes, the primary purpose of the dental material is remedying a defect in a tooth and preventing future decay. Such dental materials are known and a more detailed description can be found in U.S. Pat. Nos. 6,020,395; 6,121,344; and 6,593,395, which are each incorporated herein by reference in their respective entireties.

Dental compositions in accordance with the present invention include a plurality of nanodiamond particles. The nanodiamond particles can provide additional mechanical strength, as well as an appearance which approximates natural enamel when dry. In several embodiments of the present invention, the nanodiamond particles can be present in the composition at from about 1 wt % to about 60 wt %, and preferably from about 10 wt % to about 40 wt %.

In addition to mechanical strength, introduction of nanodiamond particles to a composition can provide a number of beneficial properties. One of such beneficial properties is an impressive ability of nanodiamonds to absorb oil and other organic materials. Carbon atoms are very small (about 1.5 angstroms); thus, various forms of carbon can pack to form a high atomic concentration. In fact, diamond has the highest atomic concentration (176 atom/nm$^3$) of all known materials. This high atomic concentration contributes to the exceptional hardness of diamond. As a result, any given surface area of a nanodiamond particle can include many more atoms than other nanoparticles of the same size.

Diamond is among the most inert materials known. Specifically, at temperatures below about 500° C., diamond typically does not react with other materials. Further, diamond is compatible with most biological systems. This is due, at least in part, to the sp$^3$ bonding of diamond and the similar bonding of most biological materials containing roughly around 25% carbon in sp$^3$ bonding. As such, diamond is ideal for use in medical applications, e.g., artificial replacements (joint coatings, heart valves, etc.), and will not deteriorate over time.

Although diamond is highly stable, if the nanodiamond surface is free of adsorbent or absorbent, i.e. clean, it is thought that carbon atoms on the surface contain unpaired electrons that are highly reactive. As a result, nanodiamond particles can readily bond to and effectively absorb a variety of atomic species. For example, small atoms such as H, B, C, N, O, and F can be readily adsorbed on the nanodiamond surface, although other atoms can also be absorbed. Hence, nanodiamond particles, with their vast number of surface atoms, can hold a large amount of such adsorbed atoms. For example, nanodiamond particles are capable of absorbing almost as many hydrogen atoms as the number of carbon atoms. Thus, nanodiamond particles can be used as storage sites for hydrogen. In addition, those small atoms are building blocks, e.g., H, CO, OH, COOH, N, CN and NO, of organic materials including biological molecules. Consequently, nanodiamond particles can readily attach to amino acids, proteins, cells, DNA, RNA, and other biological materials, and nanodiamond particles can be used to remove skin oils, facial oils, compounds that result in body odor, bacteria, etc.

Further, nanodiamonds are typically smaller than most viruses (10 to 100 nm) and bacteria (10 to 100 μm). Therefore, nanodiamond can be used to penetrate the outer layers of viruses and bacteria and then attach to RNA, DNA or other groups within the organism to prevent the virus or bacteria from functioning. Similarly, nanodiamond can be used in conjunction with known drug delivery mechanisms to treat cancer or acquired immune deficiency syndrome.

Thus, in one aspect of the present invention, a method of binding biological molecules can include formulating a nanodiamond composition containing a plurality of nanodiamond particles. The nanodiamond particles can be dispersed in a biologically acceptable carrier. The nanodiamond composition can then be contacted with a biological material such that at least a portion of the biological material is bonded to the nanodiamond composition. Examples of biological materials include organic oils, sebum, bacteria, epithelial cells, amino acids, proteins, DNA, and combinations thereof. Once the biological material is bonded to nanodiamond, the nanodiamond composition can be removed from the surface or environment. The nanodiamond composition can then be discarded or further treated to identify or otherwise utilize the absorbed biological material. In one embodiment, the nanodiamond composition can be formulated as any of the following products: deodorant, toothpaste, shampoo, antibiotic, dermal strip, DNA test strip, or skin cleanser.

Similarly, in one aspect, nanodiamond compositions of the present invention can be remedial healthcare compositions formulated for skin care. Non-limiting examples of skin care formulations include lotions, facial tissue lotion, deodorant, dermal strip, skin cleanser, soap, antibiotic, and exfoliant. Alternatively, the remedial healthcare composition can be formulated as toothpaste, shampoo, or other similar product.

In one embodiment of the present invention, the remedial healthcare composition can be formulated as a lotion. The lotion can include an acceptable carrier and a plurality of nanodiamond particles. Acceptable carriers are known in the art and can include, for example, glycerin, alcohols, water, gels, combinations of these materials, and other known carriers. In addition, the lotion can include additives such as fragrance, colorants, vitamin E, herbal supplements, antibiotics, UV absorbers, sun-block agents, and the like. A more detailed description of various lotions can be found in U.S. Pat. Nos. 6,207,175 and 6,248,339, which are each incorporated herein by reference in their respective entireties. In these embodiments of the present invention, the nanodiamond particles can be present in the composition at from about 1 wt % to about 40 wt %, and preferably from about 2 wt % to about 15 wt %.

In a similar embodiment, the remedial healthcare composition can be formulated as a lotion for application in a facial tissue. The facial tissue lotion can include an acceptable carrier and a plurality of nanodiamond particles. Acceptable carriers are known in the art and can include, for example, glycerin, alcohols, water, gels, combinations of these materials, and other known carriers. In addition, the lotion can include additives such as fragrance, colorants, vitamin E, herbal supplements, antibiotics, UV absorbers, sun-block agents, and the like. A more detailed description of facial lotion formulations can be found in U.S. Pat. No. 6,428,794, which is incorporated herein by reference in its entirety. The presence of nanodiamond particles can improve absorption of oils and undesirable deposits from the skin without abrasiveness associated with larger diamond particles. The nanodiamonds can be present in the facial tissue lotion composition at from about 1 wt % to about 30 wt %, and preferably from about 2 wt % to about 15 wt %.

In another embodiment of the present invention, the remedial healthcare composition can be formulated as a deodorant. The deodorant can include an acceptable carrier and a plurality of nanodiamond particles. Acceptable carriers can vary considerably depending on the specific formulation. For example, deodorants can be formulated as a solid, gel, cream or the like. Suitable carriers can include, but are not limited to, dimethicones, silicone fluids (e.g., siloxanes), glycerin, alcohols, water, gels, sorbitols, and other known carriers. In addition, the deodorant can include additives such as fragrance, stabilizing agents, pH or buffer agents, solvents, antiperspirant agents, and the like. A more detailed description of various deodorant formulations can be found in U.S. Pat. Nos. 5,968,490; 6,358,499; and 6,503,488, which are each incorporated herein by reference in their respective entireties. When included in deodorant compositions, the nanodiamond particles can be present in the composition at from about 1 wt % to about 40 wt %, and preferably from about 2 wt % to about 20 wt %.

In yet another embodiment of the present invention, the remedial healthcare composition can be formulated as a dermal strip. Dermal strips are typically formed having a backing substrate with an oil or sebum absorbing composition coated thereon or within the substrate. The dermal strip can include an acceptable carrier and a plurality of nanodiamond particles on the substrate. Acceptable carriers are known in the art and can include, for example, hemp, pulp papers, porous polymeric thermoplastics, and other known carriers. Additives such as herbal extracts, vitamins, antibiotics, anti-inflammatories, fragrance, and the like can also be included. A more detailed description of dermal strips can be found in U.S. patent application Ser. No. 2003/0211954 and U.S. Pat. Nos. 5,985,300; 6,106,818; and 6,607,719, which are each incorporated herein by reference in their respective entireties. In these embodiments of the present invention, the nanodiamond particles can be present in the composition at from about 1 wt % to about 40 wt %, and preferably from about 2 wt % to about 15 wt %.

In a slightly different embodiment of the present invention, the remedial healthcare composition can be formulated as a skin cleanser. The skin cleanser can include an acceptable carrier and a plurality of nanodiamond particles. Acceptable carriers are known in the art and can include, for example, glycerin, alcohols, collagen, elastin, gels, copolymeric materials, and other known carriers. In addition, the skin cleanser can include additives such as fragrance, colorants, vitamin E, herbal supplements, antibiotics, UV absorbers, hydrating agents, sun-block agents, exfoliating agents, and the like. A more detailed description of various skin cleansers can be found in U.S. Pat. Nos. 3,944,506; 4,048,123; 4,737,307; and 6,518,228, which are each incorporated herein by reference in their respective entireties. In these embodiments of the present invention, the nanodiamond particles can be present in the skin cleanser composition at from about 1 wt % to about 50 wt %, and preferably from about 5 wt % to about 30 wt %.

In one embodiment of the present invention, the remedial healthcare composition can be formulated as an antibiotic composition. Such antibiotic compositions can be formed as a skin cleanser, lotion, wound dressing, and the like similar to the other compositions described herein. U.S. Pat. Nos. 6,187,327 and 6,579,516, which are incorporated herein by reference, describe several suitable carriers and types of compositions which can be used in connection with the present invention. Including nanodiamonds in antibiotic and lotion compositions can also increase healing of skin and removal of damaged skin such as with sunburns and scar tissue.

Alternatively, the remedial healthcare composition can be formulated as toothpaste including an acceptable carrier and a plurality of nanodiamond particles. Basic formulation of toothpastes is known in the art. Common acceptable carriers can include, for example, glycerin, sorbitol, silicas (e.g., amorphous, hydrated, etc.), thickening agents such as carrageenan and salts of cellulose ethers, alcohols, water, gels, combinations of these materials, and other known carriers. In addition, the toothpaste can include additives such as sodium fluoride, fragrance, flavors, colorants, herbal supplements, and the like. A more detailed description of various toothpaste formulations can be found in U.S. Pat. Nos. 4,414,199; 6,117,415; and 6,123,925, which are each incorporated herein by reference in their respective entireties. In these embodiments of the present invention, the nanodiamond particles can be present in the composition at from about 1 wt % to about 40 wt %, and preferably from about 2 wt % to about 15 wt %.

The remedial healthcare compositions of the present invention can also be formulated as a shampoo. The shampoo can include an acceptable carrier and a plurality of nanodiamond particles. Acceptable carriers are known in the art and can include, for example, surfactants, alcohols, water, glycerin, gels, combinations of these materials, and other known carriers. In addition, the shampoo can include additives such as fragrance, colorants, vitamin E, herbal supplements, and the like. A more detailed description of various shampoos can be found in U.S. Pat. Nos. 5,326,483 and 6,306,805, which are each incorporated herein by reference in their respective entireties. In these embodiments of the present invention, the nanodiamond particles can be present in the composition at from about 1 wt % to about 40 wt %, and preferably from about 2 wt % to about 15 wt %.

Optional bubbling agents can also be added to the nanodiamond compositions of the present invention. Suitable bubbling agents can be included to increase contact of unsaturated nanodiamonds with a biological material. For example, over time, nanodiamond particles near a surface can become saturated with biological or other material. The presence of vapor bubbles can improve the rate at which such saturated nanodiamonds are removed from a surface. This can be advantageous in maximizing the effect of nanodiamonds in skin cleansers, deodorants, shampoos, soaps, toothpaste, and the like.

In another aspect of the present invention, a cosmetic nanodiamond composition can be formulated including a cosmetically acceptable carrier and a plurality of nanodiamond particles dispersed in the carrier with a dispersant. For example, the cosmetic composition can be formulated as a nail polish, eyeliner, lip gloss, or exfoliant.

Preferably, the cosmetic nanodiamond composition can be formulated as a nail polish. A nanodiamond nail polish composition of the present invention can include a cosmetically acceptable carrier and a plurality of nanodiamonds dispersed therein. Additives can also be included such as, but not limited to, dispersant, pigment, plasticizer, bubbling agent, solvent, stabilizer, UV stabilizer, moisturizers, fragrances, and combinations thereof. Additional considerations and materials for nail enamel compositions generally are discussed in U.S. patent application No. 2003/0064086 and U.S. Pat. Nos. 5,725,866; 5,882,636; and 6,352,687, which are incorporated herein by reference in their entireties. In one specific embodiment, the nanodiamond nail composition can include a polymeric resin, plasticizer, pigment, nanodiamonds, dispersant, solvent, and a UV stabilizer.

Suitable cosmetically acceptable carriers can include, but are not limited to, polymeric resins such as nitrocellulose resins, cellulose acetate resins, vinyl resins, acrylate resins, polyester resins, aldehyde derivatives such as tosylamide/formaldehyde resins, and other similar polymeric resins. Other resins can also be used which provide mechanical strength to the nail composition upon drying. Typically, such carriers can comprise from about 5 wt % to about 60 wt % of the nanodiamond nail polish composition.

Many of the above listed cosmetically acceptable carriers are somewhat rigid. Thus, softer resins can be combined with more rigid resins in order to provide mechanically sound nail enamel with some degree of flexibility. Additionally, optional plasticizers can be added to further increase the flexibility of the nail enamel upon drying. Addition of such softer resins and plasticizers can reduce premature cracking and chipping. Examples of suitable plasticizers can include benzoates, stearates, phosphates such as tricresyl phosphate, phthalates such as dibutyl phthalate and dioctyl phthalate, camphor, and the like.

The nanodiamond nail compositions typically include a solvent which provides a fluid, or spreadable composition that is suitable for application to a nail. The solvent then evaporates once applied to provide a durable hardened film on the nail, wherein the resin acts as a binder for the remaining components, e.g., pigments, nanodiamonds, etc. Non-limiting examples of common solvents which are suitable include acetates such as butyl acetate and ethyl acetate, alcohols such as isopropyl alcohol, ketones, toluene, xylene, and combinations of these solvents. One of the primary purposes of nail compositions can be to provide an aesthetically pleasing appearance. Specifically, various additives can be included which provide a wide range of colors and/or effects to the applied nail composition. For example, pigments can be included which provide a specific color to the applied nail composition. Organic pigments are most common; however, inorganic pigments can also be used. Such pigments are well known in the art and can be chosen accordingly to provide a desired color and consistency. Optional particulate materials such as mica, metal oxides, diamonds and the like can be added to provide a sparkle or other effects. For example, larger particulates create a sparkle appearance, while progressively smaller particulates can create a shimmer, or even pearlescent appearance.

The cosmetic nanodiamond composition can also include a dispersant such as those discussed above. One specific suitable dispersant for nanodiamond nail compositions which can be used in the present invention is stearalkonium hectorite.

In addition to the above-recited advantages of including nanodiamond particles in a nail formulation, the nanodiamond particles can also improve the durability of the applied nail compositions. Specifically, nanodiamonds can provide increased resistance to chipping and wear, e.g., typically a nanodiamond nail polish can last from about three to ten times longer than typical nail lacquer formulations. The nanodiamonds can be included in the cosmetic nanodiamond compositions of the present invention at about 1 wt % to about 50 wt % of the composition, and preferably from about 2 wt % to about 30 wt %.

EXAMPLE

The following example is provided in order to promote a more clear understanding of certain embodiments of the invention, and is in no way meant as a limitation thereon.

A nail polish composition is prepared including 20 wt % nitrocellulose resin, 20 wt % ethyl acetate, 25 wt % toluene and 10 wt % isopropyl alcohol solvents, 9 wt % dibutyl phthalate plasticizer, 5 wt % stearalkonium hectorite, and 3 wt % benzophenone UV stabilizer. The remaining weight percent includes an aqueous aluminum chloride suspension of 60 wt % nanodiamond particles.

It is to be understood that the above-described compositions and methods are only illustrative of preferred embodiments of the present invention. Numerous modifications and alternative arrangements may be devised by those skilled in the art without departing from the spirit and scope of the present invention and the appended claims are intended to cover such modifications and arrangements.

Thus, while the present invention has been described above with particularity and detail in connection with what is presently deemed to be the most practical and preferred embodiments of the invention, it will be apparent to those of ordinary skill in the art that numerous modifications, including, but not limited to, variations in materials, temperature, function, order, and manner of operation, assembly and use may be made without departing from the principles and concepts set forth herein.

What is claimed is:

1. A remedial healthcare nanodiamond composition, comprising:
   a) a biologically acceptable carrier; and
   b) a plurality of nanodiamond particles dispersed in the carrier with a dispersant, said nanodiamond particles having an average size of from about 0.5 nm to about 50 nm.

2. The remedial composition of claim 1, wherein the dispersant comprises from about 1 wt % to about 30 wt % of the composition.

3. The remedial composition of claim 1, wherein the dispersant is selected from the group consisting of anionic surfactants, electrolytes, alcohols, metal chlorides, metal nitrates, viscous biologically acceptable carriers, and mixtures thereof.

4. The remedial composition of claim 1, wherein the composition is a dental filling with the biologically acceptable carrier selected from composite resins, polymeric resins, ceramics, and mixtures thereof.

5. The remedial composition of claim 1, wherein the composition is a lotion with the biologically acceptable carrier selected from glycerin, alcohol, water, gels, and mixtures thereof.

6. The remedial composition of claim 1, wherein the composition is a deodorant with the biologically acceptable carrier selected from dimethicones, silicon fluids, glycerin, alcohols, water, gels, sorbitols, and mixtures thereof 7. The remedial composition of claim 1, wherein the plurality of nanodiamond particles comprise from about 1 wt % to about 60 wt % of the composition.

8. The remedial composition of claim 1, wherein the plurality of nanodiamond particles have an average size from about 0.5 nm to about 10 nm.

9. The remedial composition of claim 8, wherein the plurality of nanodiamond particles have an average size from about 0.5 nm to about 8 nm.

10. A cosmetic nanodiamond composition, comprising:
    a) a cosmetically acceptable carrier; and
    b) a plurality of nanodiamond particles dispersed in the carrier with a dispersant, said nanodiamond particles having an average size of from about 0.5 nm to about 50 nm.

11. The cosmetic composition of claim 10, wherein the composition is a member selected from the group consisting of nail polish, eyeliner, lip gloss, and exfoliant.

12. The cosmetic composition of claim 11, wherein the composition is a nail polish.

13. The cosmetic composition of claim 12, further comprising additives selected from The group consisting of dispersant, pigment, plasticizer, bubbling agent, solvent, stabilizer, and combinations thereof.

14. The cosmetic composition of claim 12, wherein the dispersant is stearalkonium hectorite.

15. The cosmetic composition of claim 10, wherein the plurality of nanodiamond particles comprise from about 1 wt % to about 50 wt % of the composition.

16. The cosmetic composition of claim 10, wherein the plurality of nanodiamond particles have an average size from about 0.5 nm to about 10 nm.

17. The cosmetic composition of claim 16, wherein the plurality of nanodiamond particles have an average size from about 0.5 nm to about 8 nm.

18. The nanodiamond composition of either of claims 1 or 10, wherein the plurality of nanodiamond particles are produced by shock wave synthesis.

19. A method of binding biological molecules, comprising the steps of:
    a) formulating a nanodiamond composition containing a plurality of nanodiamond particles dispersed in a biologically acceptable carrier; and
    b) contacting a biological material with the nanodiamond composition such that at least a portion of the biological material becomes bonded to the nanodiamond composition.

20. The method of claim 19, further comprising the step of removing the. nanodiamond composition containing biological material.

21. The method of claim 19, wherein the plurality of nanodiamond particles have an average size from about 0.5 nm to about 50 nm.

22. The method of claim 21, wherein the plurality of nanodiamond particles have an average size from about 0.5 nm to about 10 nm.

23. The method of claim 19, wherein the plurality of nanodiamond particles comprise from about 1 wt % to about 60 wt % of the nanodiamond composition.

24. The method of claim 19, wherein the nanodiamond composition is a member selected from the group consisting of deodorant, toothpaste, shampoo, antibiotic, dermal strip, DNA test strip, and skin cleanser 25. The method of claim 24, wherein the nanodiamond composition is a skin cleanser with a biologically acceptable carrier selected from glycerin, alcohols, collagen, elastin, gels, copolymeric materials, and mixtures thereof.

26. The method of claim 24, wherein the nanodiamond composition is a deodorant formulated as a solid, gel, or cream.

27. The method of claim 19, wherein said biological material is selected from the group consisting of organic oils, sebum, bacteria, epithelial cells, amino acids, proteins, DNA, and combinations thereof.

* * * * *